United States Patent
Sugrim et al.

(10) Patent No.: US 9,164,035 B2
(45) Date of Patent: Oct. 20, 2015

(54) DISTRIBUTIVE TRANSMISSOMETER

(71) Applicants: Chandraika Sugrim, Lexington Park, MD (US); Rollie DeWayne Berry, Lexington Park, MD (US); Gerald Ferguson, Chestertown, MD (US)

(72) Inventors: Chandraika Sugrim, Lexington Park, MD (US); Rollie DeWayne Berry, Lexington Park, MD (US); Gerald Ferguson, Chestertown, MD (US)

(73) Assignee: The United States of America as represented by the Secretary of the Navy, Washington, DC (US)

(*) Notice: Subject to any disclaimer, the term of this patent is extended or adjusted under 35 U.S.C. 154(b) by 13 days.

(21) Appl. No.: 14/182,815

(22) Filed: Feb. 18, 2014

(65) Prior Publication Data

US 2015/0233825 A1     Aug. 20, 2015

(51) Int. Cl.
*G01N 21/00* (2006.01)
*G01N 21/59* (2006.01)
*G01N 15/14* (2006.01)

(52) U.S. Cl.
CPC ............ *G01N 21/59* (2013.01); *G01N 15/1434* (2013.01); *G01N 2201/062* (2013.01); *G01N 2201/06113* (2013.01)

(58) Field of Classification Search
CPC ..... G01N 21/538; G01N 21/59; G01N 29/02; G01N 33/2888; G01N 15/0205; G01N 15/1459; G01N 2021/035; G01N 21/05; G01N 21/255; G01N 21/5907; G01N 2201/0224; G01N 33/1886; G01N 33/246; G01N 33/28
See application file for complete search history.

(56) References Cited

U.S. PATENT DOCUMENTS

| | | | |
|---|---|---|---|
| 5,444,530 A | * | 8/1995 | Wang .............................. 356/338 |
| 2003/0038940 A1 | * | 2/2003 | Metcalfe et al. .............. 356/437 |
| 2003/0174317 A1 | * | 9/2003 | Murdock et al. ............. 356/218 |
| 2011/0317161 A1 | * | 12/2011 | Roy et al. ...................... 356/336 |

* cited by examiner

*Primary Examiner* — Michael P Stafira
(74) *Attorney, Agent, or Firm* — Mark O. Glut; NAWCAD

(57) ABSTRACT

A distributive transmissometer, comprising a series of light sources that illuminate and map out a volume of space to be sampled to a one-dimensional space, a light detector, the one-dimensional space being mapped to the light detector such that spatial dust density distribution of the volume to be sampled can be determined; and, a lens for focusing light emitted by the light sources toward the light detector.

3 Claims, 1 Drawing Sheet

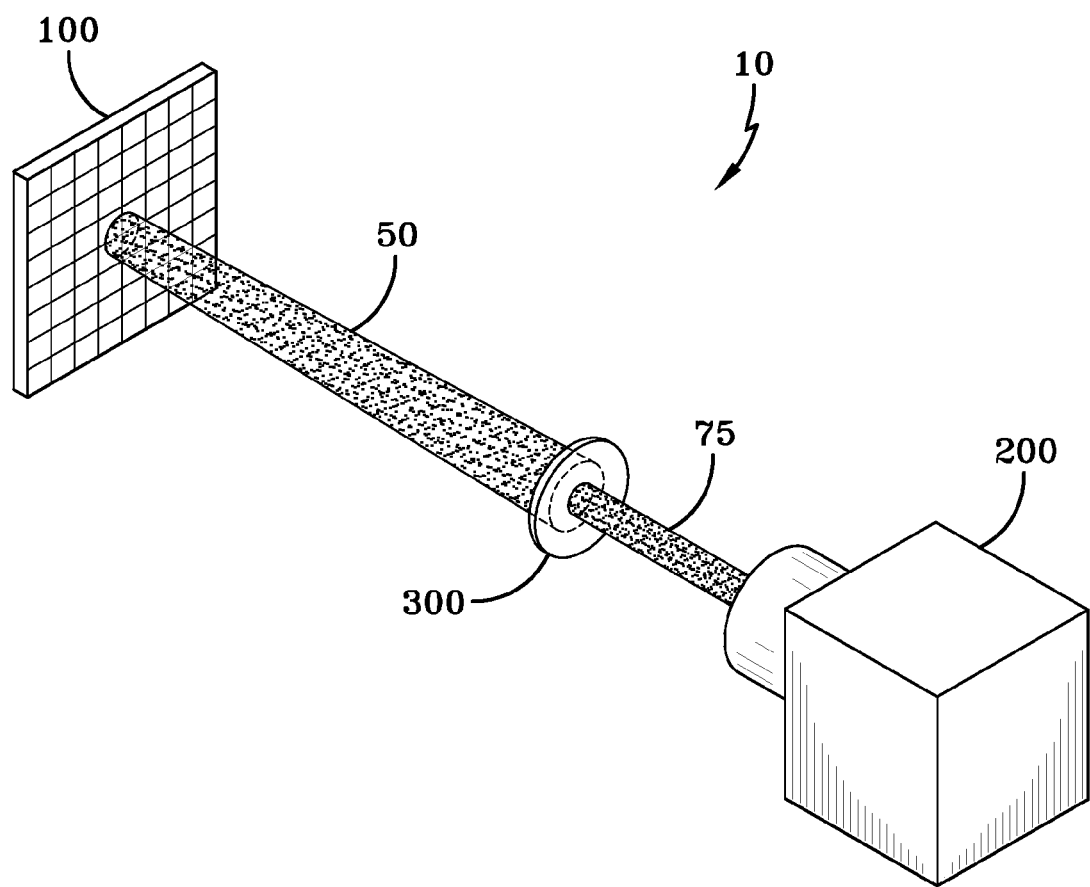

DISTRIBUTIVE TRANSMISSOMETER

STATEMENT OF GOVERNMENT INTEREST

The invention described herein may be manufactured and used by or for the Government of the United States of America for governmental purposes without payment of any royalties thereon or therefor.

BACKGROUND

A transmissometer may be described as, but without limitation, an instrument for measuring the extinction coefficient of the atmosphere and for the determination of visual range. A tranmissometer typically operates by sending a narrow, collimated beam of energy (usually a laser) through a propagation medium. A narrow field of view receiver at the designated measurement distance determines how much energy is arriving at the detector, and determines the path transmission and/or extinction coefficient. Transmissometers may be referred to, but without limitation, as telephotometers, transmittance meters, or hazemeters.

Currently there is no commercial apparatus available to provide real time spatial dust density distribution in a large volume. Point sampling transmissometers are sometimes used; however, the spatial samplings from these types of transmissometers are finite and typically limited by beam and detector size. Additionally, the spatial resolution provided by point sampling transmissometers is limited.

SUMMARY

The present invention is directed to a distributive transmissometer that meets the needs enumerated above and below.

The present invention is directed to a distributive transmissometer which includes a series of light emitting diodes, an imaging device, and a lens. The series of light emitting diodes illuminate and map out a volume of space to be sampled to a one-dimensional space. The one-dimensional space is mapped to the imaging device such that spatial dust density distribution of the volume to be sampled can be determined The lens is for focusing light emitted by the light emitting diodes toward the imaging device.

It is a feature of the present invention to provide a distributive transmissometer which provides real time spatial dust density distribution in a large volume.

It is a feature of the present invention to provide a distributive transmissometer with good spatial resolution.

DRAWINGS

These and other features, aspects and advantages of the present invention will become better understood with reference to the following description and appended claims, and accompanying drawings wherein FIG. 1 is an embodiment of the distributive transmissometer.

DESCRIPTION

The preferred embodiments of the present invention are illustrated by way of example below and in FIG. 1. As shown in FIG. 1, a distributive transmissometer 10 includes a series of light sources 100, a light detector system or imaging device 200, and a lens 300. The series of light sources 100 illuminate and map out a volume of space 50 to be sampled to a one-dimensional space. The one-dimensional space is mapped to the light detector system 200 such that spatial dust density distribution of the volume 50 to be sampled can be determined The lens 300 is for focusing light 75 emitted by the light sources 100 toward the light detector system 200.

In the description of the present invention, the invention will be discussed in a military environment; however, this invention can be utilized for any type of application that requires use of transmissometer.

The series of light sources 100 may be a series of light emitting diodes constructed using a series of LED/LASER light sources to reference a volume 50 of space being interrogated. The light detector 200 is a system which measures the intensity of the series of light sources 100 for each section of spatial volume under investigation without any obscurant/scatter being present. The light detector system 200 may be, but without limitation, an imaging system such as a CCD camera. The measurement obtained by the light detector system 200 is now the "baseline intensity measurement" for what is called a "Clear Air" sample. As obscurant/particulate is being introduced to these spatial volumes, the light intensities would diminish. Even as the light intensities diminish, the light detector system 200 will continue to sample the spatial volumes for their new intensities values.

With the new intensities and baseline intensity values, the transmittance values for each spatial volume is calculated ($I_{new}/I_{baseline}$). From the transmittance value and the known distance of the light source 100 to the light detector system 200, the quantity of particulates in each volume is calculated. This relationship is given by Beer-Lamberet's Law shown in Equation 1 below:

$$T = e^{-\alpha CL}, \qquad \text{Equation 1}$$

where T is the transmittance measured by the transmissometer, $\alpha$ is the mass extinction coefficient, C is the concentration of obscurant/particulate in that volume at a distance L from the detector system. The mass extinction coefficient term $\alpha$ is determined experimentally, but remains static for the remainder of measurements in this environment. Knowing the transmittance, the mass extinction coefficient and the distance from the light sources 100 are from the light detector system 200, the concentration of obscurant/particulates may be calculated, determining the spatial dust density distribution of the volume to be sampled.

In one of the embodiments of the invention, the physical implementation of this system is to use a point-like source such as a LED/LASER and let the beam diverge as it samples the volume that it is propagating through. This spatial sampling is then recorded with an imaging system, such as CCD array that records the spatial intensity for said volume. By multiplexing through the LEDS/LASERS array, a spatial map of the transmittance is then created using the baseline values and the newly acquired intensities. From these transmittance measurements, the concentration for each spatial volume is then determined These measurements are taken real time with no perturbation of the environmental conditions.

The reason that the LED/LASERs are multiplexed is to eliminate the cross talk between spatial volumes being sampled. Additionally, this provides more detector surface used to gather light intensity for each volume. It can also be used to cut down on the background noise introduced by the ambient environment. In this particular situation the bias on said detector system can be turned on when only a LED/LASER is turned on.

The results of each LED/LASER strobed unto the CCD array are stored onto bitmaps. The ratio of the new intensities and clear air intensities from these bitmap provides the transmittance value. The reason bitmaps are chosen is bitmaps capture each pixel (on the camera) digital value that represents the intensity that that the pixel is exposed to. In essence, the camera is acting like a power meter with a digitizer. Because we are not interested in the absolute power measurement, this method of digitizing the optical power measurement is sufficient to determine the mass concentration.

When introducing elements of the present invention or the preferred embodiment(s) thereof, the articles "a," "an," "the," and "said" are intended to mean there are one or more of the elements. The terms "comprising," "including," and "having" are intended to be inclusive and mean that there may be additional elements other than the listed elements.

Although the present invention has been described in considerable detail with reference to certain preferred embodiments thereof, other embodiments are possible. Therefore, the spirit and scope of the appended claims should not be limited to the description of the preferred embodiment(s) contained herein.

What is claimed is:

1. A distributive transmissometer, comprising:
    a series of light sources that illuminate and spatially map out a volume of space to be sampled to a one-dimensional space;
    a light detector, the one-dimensional space being mapped to the light detector and spatially multiplexed such that concentration ($g/m^3$) of spatial dust density distribution of the volume to be sampled can be determined; and,
    a lens for focusing light emitted by the light sources toward the light detector.

2. The distributive transmissometer of claim 1, wherein the series of light sources is a series of light emitting diodes.

3. The distributive transmissometer of claim 1, wherein the series of light sources is a system of LED/LASER lights.

* * * * *